United States Patent [19]
Li et al.

[11] Patent Number: 6,093,799
[45] Date of Patent: Jul. 25, 2000

[54] UNIVERSAL LINKER FOR COMBINATORIAL SYNTHESIS

[75] Inventors: Ge Li, Lawrenceville; Sian Louise Griffiths, Plainsboro; Edward McDonald, Lawrenceville; Libo Xu, Plainsboro, all of N.J.

[73] Assignee: Pharmacopeia, Inc., Princeton, N.J.

[21] Appl. No.: 09/421,732

[22] Filed: Oct. 20, 1999

Related U.S. Application Data

[62] Division of application No. 09/039,837, Mar. 16, 1998, Pat. No. 6,008,321.
[51] Int. Cl.$^7$ ..................... G01N 33/543; G01N 33/545; C07C 59/48; C07C 59/56; C07C 231/00
[52] U.S. Cl. .................... 530/334; 436/531; 436/518; 436/523; 530/335; 562/426; 562/431; 562/466; 562/471; 562/472; 564/123; 564/161; 564/162; 564/163; 568/583; 568/626; 568/630; 568/667
[58] Field of Search .............................. 436/518, 523–31; 530/334, 335; 562/426, 431, 466, 471, 472; 564/123, 161–163; 568/583, 626, 630, 667

*Primary Examiner*—Bennett Celsa
*Assistant Examiner*—Maurie E. Garcia
*Attorney, Agent, or Firm*—Heslin & Rothenberg, P.C.

[57] ABSTRACT

A substrate for solid phase synthesis of the formula:

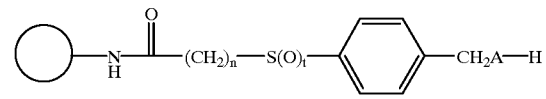

is disclosed. Also disclosed are processes for preparing the substrate and intermediates useful therein. Among the novel intermediates are compounds of the formula:

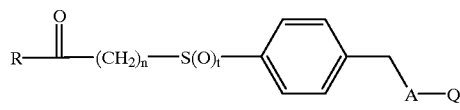

wherein t is 0 or 1; n is 3–20; R is OH, an activated ester or the residue of a solid support having a plurality of amino functionalities; A is —O— or —NH— and Q is hydrogen or a protecting group for an amine or alcohol.

14 Claims, No Drawings

UNIVERSAL LINKER FOR COMBINATORIAL SYNTHESIS

CROSS REFERENCE TO RELATED APPLICATIONS

This application is a divisional of U.S. application, Ser. No. 09/039,837, filed Mar. 16, 1998, now U.S. Pat. No. 6,008,321 the entire disclosure of which is incorporated herein by reference.

TECHNICAL FIELD

This invention relates generally to the synthesis of chemical compounds, and more particularly, to the solid phase synthesis of combinatorial libraries of chemical compounds.

BACKGROUND OF THE INVENTION

Combinatorial organic synthesis is becoming an important tool in drug discovery. Methods for the synthesis of large numbers of diverse compounds have been described [Ellman, et. al. *Chem. Rev.* 96: 555–600 (1996)], as have methods for tagging systems [Ohlmeyer et al., *Proc. Natl. Acad. Sci. USA*, 90, 10922–10926, (1993)]. The growing importance of combinatorial synthesis has created a need for new resins and linkers having chemical and physical properties to accommodate a wide range of conditions, since success depends on the ability to synthesize diverse sets of molecules on solid supports and to then cleave those molecules from the supports cleanly and in good yield.

Linkers are molecules that can be attached to a solid support and to which the desired members of a library of chemical compounds may in turn be attached. When the construction of the library is complete, the linker allows clean separation of the target compounds from the solid support without harm to the compounds and preferably without damage to the support. Several linkers have been described in the literature. Their value is constrained by the need to have sufficient stability to allow the steps of combinatorial synthesis under conditions that will not cleave the linker, while still having a fairly high liability under at least one set of conditions that is not employed in the synthesis. For example, if an acid labile linker is employed, then the combinatorial synthesis must be restricted to reactions that do not require the presence of an acid of sufficient strength to endanger the integrity of the linker. This sort of balancing act often imposes serious constraints on the reactions that can be employed in preparing the library.

The 4-[4-(hydroxymethyl)-3-methoxyphenoxy]butyryl residue is a known linker, which is attached to a solid support having amino functionalities by forming an amide with the carboxyl of the butyric acid chain. N-Protected amino acids are attached to the hydroxyl of the 4-hydroxymethyl group via their carboxyl to form 2,4-dialkoxybenzyl esters, which can be readily cleaved in acid media when the synthesis is complete [see for example Riniker et al. *Tetrahedron* 49 9307–9312 (1993)]. The drawback to such 2,4-dialkoxybenzyl esters is that they can also be cleaved by many of the reagents that one night want to use in combinatorial synthesis.

A somewhat more stable ester is formed from 4-[4-(hydroxymethyl)phenoxy]buteric acid. It has been described in European published application EP 445915. In this case, the ester was cleaved with a 90:5:5 mixture of trifluoroacetic acid, dimethyl sulfide and thioanisole.

When the desired product is a peptide amide, the 4-[4-(formyl)-3,5-dimethoxyphenoxy]butyryl residue has been employed. It is attached to a solid phase substrate via the carboxyl of the butyric acid chain, and the 4-aldehyde is reductively aminated. N-Protected amino acids are then reacted with the alkylamine via their carboxyl to form 2,4,6-trialkoxybenzylamides. These may be cleaved by 1:1 trifluoroacetic acid in dichloromethane. [See PCT application WO97/23508.]

It would be useful to have a linker-resin combination that would withstand a wider range of reaction conditions in combinatorial synthesis, but that could be readily and cleanly cleaved following completion of the solid phase synthesis.

SUMMARY OF THE INVENTION

The present invention relates to a linker-resin combination that demonstrates the ability to withstand many of the common reaction conditions and yet is cleavable under relatively mild conditions. In the following disclosure, the variables are defined when introduced and retain that definition throughout.

In one aspect, the invention relates to a substrate for solid phase synthesis comprising a solid phase-linker combination of the formula:

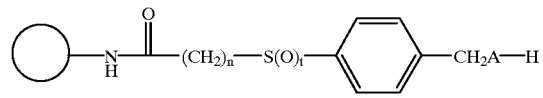

wherein

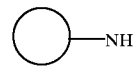

represents the residue of a solid support having a plurality of amino functionalities and the remainder constitutes the linker.;

A is —O— or —NH—;

n is 3–20, preferably 3–5; and t is 0 or 1. Preferred solid phases are aminomethylated poly(styrene-co-divinylbenzene) and divinylbenzene-cross-linked, polyethyleneglycol-grafted polystyrene functionalized with amino groups.

In another aspect, the invention relates to chemical intermediates of the formula VI

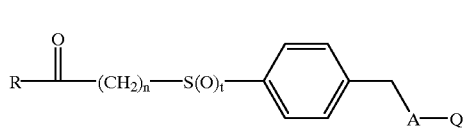

VI wherein Q is hydrogen or a protecting group for an amine or alcohol; and R is chosen from OH, the residue of a solid support having a plurality of amino functionalities, and a residue of an activated ester. Preferred activated ester residues are those of pentafluorophenol, N-hydroxysuccinimide and hydroxybenzotriazole:

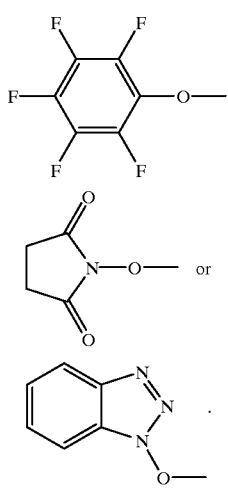

When A is NH, Q is preferably t-butoxycarbonyl or benzyloxycarbonyl; when A is —O—, Q is preferably aryl- or alkylcarbonyl (e.g. benzoyl or acetyl), benzyl, t-butyl, tetrahydropyranyl or trialkylsilyl.

In another aspect, the invention relates to processes for preparing the foregoing substrate for solid phase synthesis. One process comprises:

(a) combining in a suitable solvent a condensing agent, a solid support having a plurality of amino functionalities, and a compound of formula IV (i.e. VI in which R=OH)

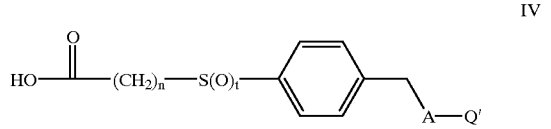

IV wherein Q' is a protecting group for an amine or alcohol to provide a protected precursor of a substrate for solid phase synthesis; and (b) treating the protected precursor with a reagent capable of cleaving the protecting group Q to provide a substrate for solid phase synthesis. In an alternative process, in step (a) a subset of VI in which R is a group displaceable by an amine ($R^4$) and no condensing agent is needed. Typically $R^4$ will be an activated ester and preferred activated esters are those shown above.

In another aspect, the invention relates to a process for solid phase synthesis comprising:

(a) reacting a substrate for solid phase synthesis of the formula:

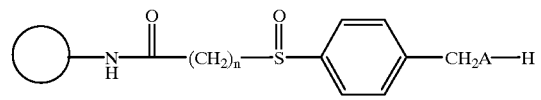

with a reagent capable of reacting with an amine or alcohol to provide a support-linked synthon;

(b) carrying out a plurality of chemical transformations on the support-linked synthon to provide a support-linked product;

(c) treating the support-linked product with a trivalent phosphorus reagent, whereby the sulfoxide is reduced to a thioether; and (d) treating the support-linked product with acid to cleave the product from the support and linker. Preferred trivalent phosphorus reagents are tributyl phosphine and triphenylphosphine. Trifluoroacetic acid is a preferred acid for cleavage.

DETAILED DESCRIPTION OF THE INVENTION

Abbreviations and Definitions

The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaminopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
MCPBA=meta-chloroperbenzoic acid
Me=methyl
mesyl=methanesulfonyl
NMO=N-methylmorpholine oxide
PEG=polyethylene glycol
Ph=phenyl
PhOH=phenol
PfP=pentafluorophenol
PyBroP=bromo-tris-pyrrolidino-phosphonium hexafluorophosphate
rt=room temperature
sat'd=saturated
s-=secondary
t-=tertiary
TBDMS=t-butyldimethylsilyl
TFA=trifluoroacetic acid
THF=tetrahydrofliran
TMOF=trimethyl orthoformate
TMS=trimethylsilyl
tosyl=p-toluenesulfonyl
Trt=triphenylmethyl "Alkyl" is intended to include linear, or branched hydrocarbon structures and combinations thereof of 1 to 20 carbons. "Lower alkyl" means alkyl groups of from 1 to 6 carbon atoms. Examples of lower allyl groups include methyl, ethyl, propyl, isopropyl, butyl, s-and t-butyl, pentyl, hexyl, and the like.

"Cycloalkyl" refers to saturated hydrocarbons of from 3 to 12 carbon atoms having one or more rings. Examples of "cycloalkyl" groups include c-propyl, c-butyl, c-pentyl, c-hexyl, 2-methylcyclopropyl, cyclopropylmethyl, cyclopentylmethyl, norbomyl, adamantyl, myrtanyl and the like. "Lower cycloalkyl" refers to cycloalkyl of 3 to 6 carbons.

$C_1$ to $C_{20}$ Hydrocarbon includes allyl, cycloalkyl, alkenyl, alkynyl, aryl and combinations thereof. Examples include phenethyl, cyclohexylmethyl and naphthylethyl.

"Alkoxy" means alkoxy groups of from 1 to 8 carbon atoms of a straight, branched, cyclic configuration and combinations thereof. Examples of alkoxy groups include methoxy, ethoxy, propoxy, isopropoxy, cyclopropyloxy, cyclohexyloxy, and the like. "Lower alkoxy" means alkoxy having 1–4 carbon atoms.

"Halo" includes F, Cl, Br, and I.

"Fluoroalkyl" refers to an alkyl residue in which one or more hydrogen atoms are replaced with F, for example: trifluoromethyl, difluoromethyl, and pentafluoroethyl.

"Arylalkyl" denotes a residue comprising an alkyl attached to an aromatic or heteroaromatic ring. Examples include benzyl, phenethyl, 4-chlorobenzyl, and the like.

For the purpose of the present invention, the term "combinatorial library" means a collection of molecules based on logical design and involving the selective combination of building blocks by means of simultaneous chemical reactions. Each species of molecule in the library is referred to as a member of the library.

As will be obvious to the person of skill in the art, the linkers of the invention could be used in combinatorial synthesis to attach tags as well as to attach the moiety of putative chemical or pharmacological interest. Tags are chemical entities which possess several properties: they are detachable from the solid supports, preferably by means orthogonal to those employed for releasing the compound of pharmacological interest; they are stable under the synthetic conditions; and they are capable of being detected in very small quantities, e.g., $10^{-18}$ to $10^{-9}$ mole. Suitable tags and methods for their employment are described in U.S. Pat. No. 5,565,324, the entire disclosure of which is incorporated herein by reference.

The materials upon which combinatorial syntheses are performed are referred to as solid supports, beads, and resins. These terms are intended to include:

(a) beads, pellets, disks, fibers, gels, or particles such as cellulose beads, pore-glass beads, silica gels, polystyrene beads optionally cross-linked with divinylbenzene and optionally grafted with polyethylene glycol, polyacrylamide beads, latex beads, dimethylacrylamide beads optionally cross-linked with N,N'-bis-acryloyl ethylene diamine, glass particles coated with hydrophobic polymer, etc., i.e., material having a rigid or semi-rigid surface; and (b) soluble supports such as polyethylene glycol or low molecular weight, non-cross-linked polystyrene. The solid supports may, and usually do, have functional groups such as amino, hydroxy, carboxy, or halo groups; amino groups are the most common. Techniques for functionalizing the surface of solid phases are well known in the art. Attachment of lysine to the amino groups on a bead (to increase the number of available sites) and subsequent attachment of linkers as well as further steps in a typical combinatorial synthesis are described, for example, in PCT application WO95/30642, the disclosure of which is incorporated herein by reference. In the synthesis described in WO95/30642, the linker is a photolytically cleavable linker, but the general principles of the use of a linker are well illustrated.

The invention relates to substrates for solid phase synthesis comprising solid phase-linker combinations of the formula:

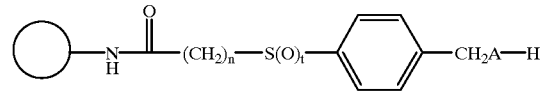

In these solid phase-linker combinations, t=1 at the beginning of solid phase synthesis and t is reduced to t=0 when it is desired that the linker can be cleaved. The relative stability of the sulfoxide (t=1) allows the use in solid phase synthesis of acids and bases that would cleave an alkylthiobenzyl linkage. We refer to these linkers as "universal linkers" because of their stability to both basic and acidic conditions. When the elaboration of the attached moiety is complete, the sulfoxide may be reduced under very mild conditions to a thioether. The thioether activates the benzyl alcohol (or amine, depending on the nature of A) toward acid cleavage. The linker can then be acid cleaved without harm to the compounds being synthesized and without damage to the support.

The solid phase-linker combinations are prepared by the following route:

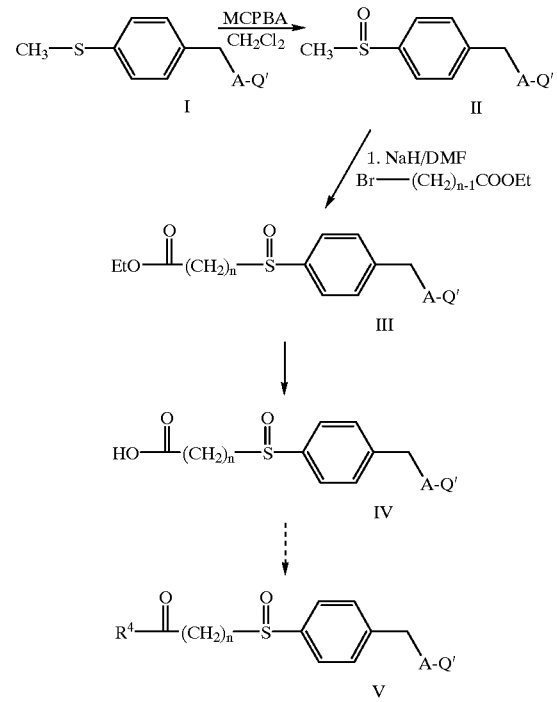

Commercially available 4-(methylthio)benzyl alcohol or benzylamine is protected with any of the well-known protecting groups for alcohols or amines. [See Greene and Wuts *Protective Groups in Organic Synthesis* Second Edition John Wiley & Sons, New York 1991, pages 1–118 and 309–370 which are incorporated herein by reference.]. Preferred protecting groups are t-butyldiphenylsilyl for the benzyl alcohol and t-BOC for the amine. Methods for protecting and deprotecting with these groups are found in Greene and Wuts on pages 83 and 327 respectively.

The suitably protected 4-(methylthio)benzyl alcohol or benzylamine I is oxidized with a slight excess of metachloroperbenzoicacid (MCPBA) in an inert solvent such as dichloromethane. Other oxidants for converting thioethers to sulfoxides are known and could be used, but MCPBA is convenient. The resulting suboxide II is deprotonated with a strong base, such as sodium hydride in DMF, and alkylated on carbon with an ω-bromoalkanoate ester of one fewer carbons than the desired chain length. Methyl and ethyl esters are preferred. An alternative route to the same ester-sulfoxide III is via the alkylation of the protected 4-mercaptobenzyl alcohol or amine with an ω-bromoalkanoate ester of the same number of carbons as the desired chain length followed by oxidation with MCPBA. Lower alkyl ω-haloalkylcarboxylates are readily prepared by procedures known in the art, and most of those in the C-4 to C-10 range are commercially available. In preferred embodiments, the lower alkyl ω-haloalkylcarboxylate is ethyl 4-bromobutyrate.

The ester III is saponified with an aqueous base, preferably an alkali metal hydroxide, such as lithium hydroxide, and the pH may be controlled, e.g. by means of an autotitrator.

The acid IV may be directly condensed with the amino functionality on the solid support, or an activated derivative V may be preformed. Condensing agents for reacting amines (the resin) with carboxylic acids (the linker) are well known, particularly in the art of solid phase synthesis of peptides. Such agents include carbodiimides of various sorts, mixed anhydrides, EEDQ, HATU, and the like. It is also possible to pre-react the carboxylic acid of the linker with an appropriate leaving group to form an activated ester. Activated esters denote esters which are capable of undergoing a substitution reaction with primary or secondary amines to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters. Solvents that are inert to the conditions of the condensation are "suitable solvents". These include, for example, THF, DMF, DCM and the like.

For combinatorial synthesis, the solid phase-linker combination may be reacted with a carboxylic acid, an alkyl halide or any other substituent known to react with an alcohol or amine. The choice of reagent is immaterial to the present invention and is determined by the nature of the combinatorial library sought to be synthesized. The number and nature of further reactions of support-linked synthon will be similarly dictated by the needs of the library. When the combinatorial synthesis is complete, the sulfoxide in the linker can be reduced with a trivalent phosphorus reagent and the linker cleaved from the resin by treatment with acid, preferably trifluoroacetic acid in dichloromethane, or HCl in diethyl ether or dioxane.

What is claimed is:

1. A substrate for solid phase synthesis comprising a solid phase-linker combination of the formula:

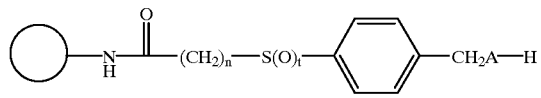

wherein

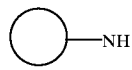

represents the residue of a solid support having a plurality of amino functionalities;
A is —O— or —NH—;
n is 3–20; and
t is 0 or 1.

2. A substrate according to claim 1 wherein n is 3–5.
3. A substrate according to claim 1 wherein

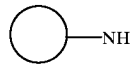

is chosen from aminomethylated poly(styrene-co-divinylbenzene) and divinylbenzene-cross-linked, polyethyleneglycol-grafted polystyrene functionalized with amino groups.

4. A process for preparing a substrate for solid phase synthesis of the formula:

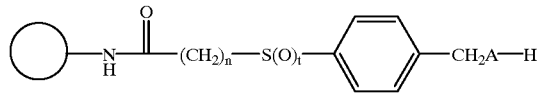

wherein

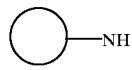

represents the residue of a solid support having a plurality of amino functionalities;
t is 1;
A is —O— or —NH—;
and n is 3–20,
comprising
(a) combining in a suitable solvent a condensing agent, a solid support having a plurality of amino functionalities, and a compound of formula

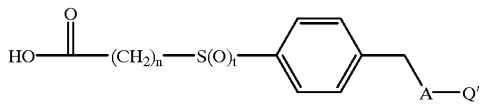

wherein Q' is a protecting group for an amine or alcohol, to provide a protected precursor of a substrate for solid phase synthesis; and
(b) treating said protected precursor of a substrate for solid phase synthesis with a reagent capable of cleaving the protecting group Q' to provide said substrate for solid phase synthesis.

5. A process according to claim 4 wherein said solid support is chosen from aminomethylated poly(styrene-co-divinylbenzene) and divinylbenzene-cross-linked, polyethyleneglycol-grafted polystyrene functionalized with amino groups.

6. A process according to claim 4 wherein n is 3–5, A is —O— and Q' is benzyl, tetrahydropyranyl or trialkylsilyl.

7. A process according to claim 4 wherein n is 3–5, A is —NH— and Q' is t-butoxycarbonyl, or benzyloxycarbonyl.

8. A process for preparing a substrate for solid phase synthesis of the formula:

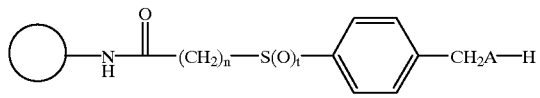

wherein

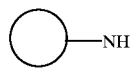

represents the residue of a solid support having a plurality of amino functionalities;

t is 1;
A is —O— or —NH—;
and n is 3–20,
comprising
(a) combining in a suitable solvent a solid support having a plurality of amino functionalities and a compound of formula

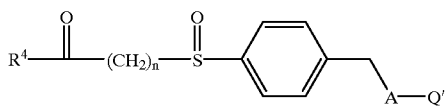

wherein $R^4$ is a group displaceable by an amine and Q' is a protecting group for an amine or alcohol to provide a protected precursor of a substrate for solid phase synthesis; and (b) treating said protected precursor of a substrate for solid phase synthesis with a reagent capable of cleaving the protecting group Q' to provide said substrate for solid phase synthesis.

9. A process according to claim 8 wherein said solid support is chosen from aminomethylated poly(styrene-co-divinylbenzene) and divinylbenzene-cross-linked, polyethyleneglycol-grafted polystyrene functionalized with amino groups.

10. A process according to claim 8 wherein n is 3–5, A is —O— and Q' is benzyl, tetrahydropyranyl or trialkylsilyl.

11. A process according to claim 8 wherein n is 3–5, A is —NH— and Q' is t-butoxycarbonyl or benzyloxycarbonyl.

12. A process for solid phase synthesis comprising:

(a) reacting a substrate for solid phase synthesis of the formula:

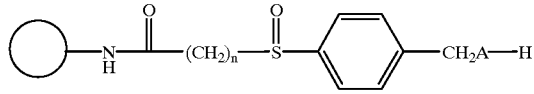

wherein

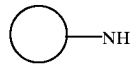

represents the residue of a solid support; A is —O— or —NH—; and n is 3–20, with a reagent capable of reacting with an amine or alcohol to provide a support-linked synthon;

(b) carrying out a plurality of chemical transformations on said support-linked synthon to provide a support-linked product;

(c) treating said support-linked product with a trivalent phosphorus reagent, whereby the sulfoxide is reduced to a thioether; and (d) treating said support-linked product with acid to cleave the product from the support and linker.

13. A process according to claim 12 wherein said trivalent phosphorus reagent is tributyl phosphine or triphenyl phosphine.

14. A process according to claim 12 wherein said acid is trifluoroacetic acid.

* * * * *